Oct. 3, 1933. V. BERGER Plant Pat. 78
ROSE
Filed Feb. 1, 1933
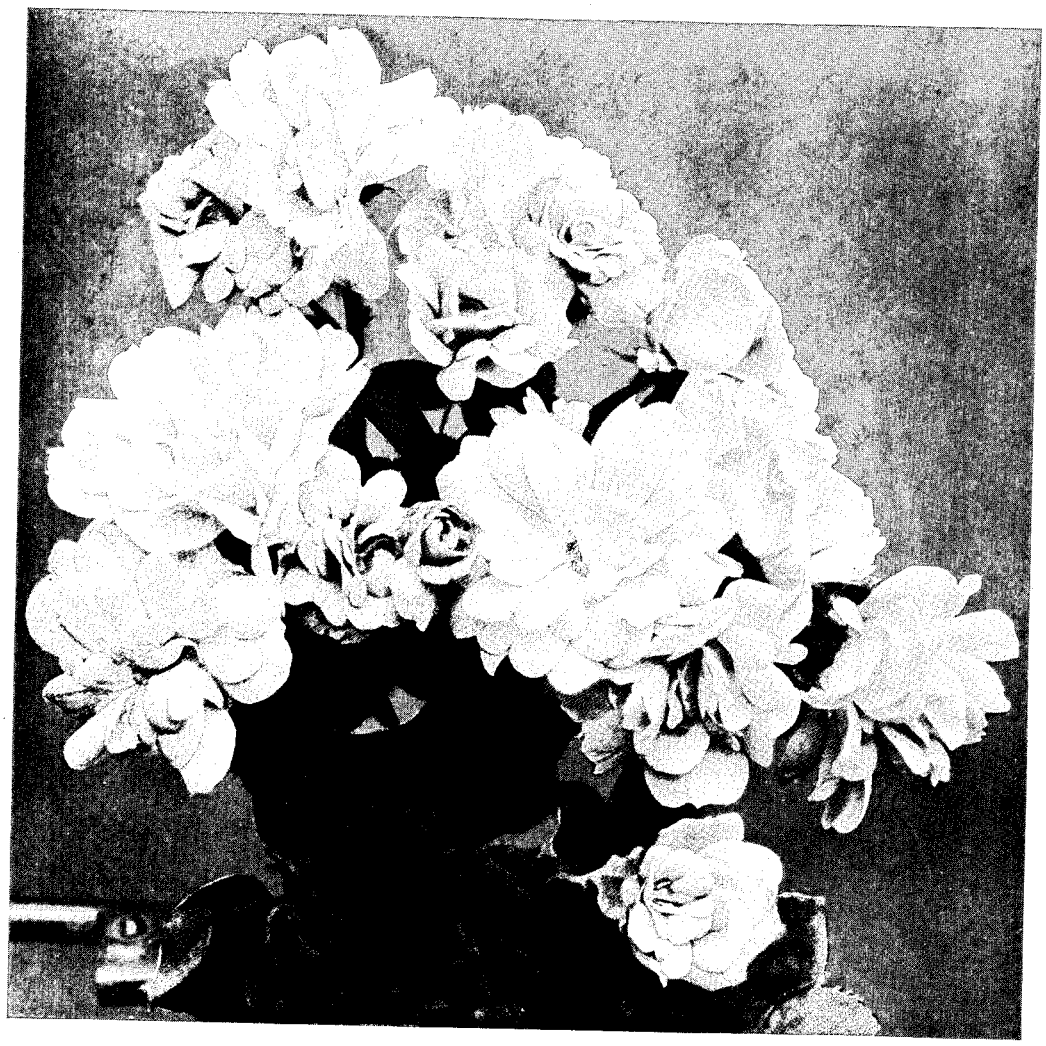
INVENTOR
Vinzenz Berger
By Orville M. Kile
PLANT PATENT AGENT Patented Oct. 3, 1933

UNITED STATES PATENT OFFICE

Plant Pat. 78

ROSE

Vinzenz Berger, Chomutov (Komotau), Czechoslovakia, assignor to Paul J. Howard, Los Angeles, Calif.

Application February 1, 1933. Serial No. 654,704

1 Claim. (Cl. 47—61)

My new variety of rose may be described as a Polyantha-Rugosa-Hybrid and is really a new class or type of rose as well as a new variety. I developed this new rose by crossing a Rugosa seedling and the Polyantha Rose named Mevrouw Natalie Nypels. The distinctive character of this new rose became apparent in the year 1930. After observing and testing this original plant for a period, I reproduced it asexually and thus determined that it would reproduce true to type.

In this new Hybrid the Rugosa character has, to a great extent, been eliminated from the flower and foliage but there has been retained the very hardy, free growing, healthy characteristics of the Rugosa making it particularly valuable for use in localities having severe climates.

The flowers begin to bloom early in the summer and continue without interruption until late fall.

The accompanying illustration shows in full color a mass of the flowers in various stages of maturity as they occur on a single plant. It must be understood, however, that while this is true illustration of an average specimen of this new variety of rose as grown in a greenhouse in the United States in the latitude of Philadelphia, when grown out of doors its flowers assume a brighter, redder color.

The plant is of vigorous growth, upright in form and branching, usually attaining a height of 40 to 50 centimeters.

The stems are strong, green and vigorous and bear a moderate number of long, sharp thorns.

The leaves are medium green in color, rather large, thick and leathery in texture, and are toothed.

The flowers are borne in clusters as well as singly. Usually there will be two to four individual flowers in a cluster. The individual flowers are well-formed, double and when fully opened measure 6 to 8 centimeters in diameter, being unusually large for a Polyantha Hybrid.

The buds are of a coppery-fire red. As the flower opens it becomes lighter in color and gradually develops a most pleasing salmon-rose color which is particularly striking late in the Autumn when the nights become cool.

There is no tendency in this variety toward the production of badly faded or purplish colors as the flowers age—an undesirable character so common in Polyantha roses.

The large mass of bright colored blossoms, of reddish and pink shades, readily distinguishes this variety at a glance, while its hardy, vigorous nature further recommends it.

Having thus disclosed my invention, I claim:

The variety of Polyantha-Rugosa-Hybrid rose herein shown and described, characterized particularly by its clusters of well-formed Polyantha-type flowers of red to pink color, combined with the vigorous, healthy, hardy Rugosa-type habits of growth.

VINZENZ BERGER.